United States Patent [19]

Dickakian

[11] Patent Number: 4,849,361
[45] Date of Patent: Jul. 18, 1989

[54] METHOD FOR CHARACTERIZING THE COKING TENDENCIES OF BASEOILS AND ADDITIVE-TREATED OILS

[75] Inventor: Ghazi B. Dickakian, Houston, Tex.

[73] Assignee: Exxon Chemical Patents Inc., Linden, N.J.

[21] Appl. No.: 876,462

[22] Filed: Jun. 20, 1986

[51] Int. Cl.⁴ .................. G01N 31/00; G01N 33/26
[52] U.S. Cl. .......................... 436/2; 73/61.2; 73/64; 436/60
[58] Field of Search .............. 422/68, 70, 69; 436/2, 436/60, 140, 141, 161, 162; 73/61.2, 61.10, 64

[56] References Cited

U.S. PATENT DOCUMENTS

| | | | |
|---|---|---|---|
| 2,302,224 | 11/1942 | Jones | 73/64 |
| 2,716,089 | 8/1955 | Cyphers et al. | |
| 2,732,285 | 1/1956 | Lynch et al. | 436/60 |
| 2,812,319 | 11/1957 | Jones | |
| 3,095,377 | 6/1963 | Hart et al. | |
| 3,153,622 | 10/1964 | Humphrey et al. | |
| 3,248,327 | 4/1966 | Whitaker | |
| 3,248,927 | 5/1966 | Buehler et al. | 436/60 |
| 4,155,833 | 5/1979 | Gleim | 208/309 |

FOREIGN PATENT DOCUMENTS 13274  6/1968  Japan .................... 436/60

*Primary Examiner*—Robert J. Hill, Jr.
*Attorney, Agent, or Firm*—S. H. Markowitz; M. B. Kapustij

[57] ABSTRACT

Method of characterizing the coking tendency of a baseoil, by:
(a) exposing the baseoil to conditions which accelerate asphaltene formation in the baseoil; and
(b) testing for the onset and/or progression of asphaltene formation as a function of time.

The technique is also useful for determining the efficacy of oil additives.

18 Claims, 6 Drawing Sheets

FIG. 2a AIR OXIDATION UNIT

FIG. 2c AIR SPARGER

METHOD FOR CHARACTERIZING THE COKING TENDENCIES OF BASEOILS AND ADDITIVE-TREATED OILS

BACKGROUND OF THE INVENTION

1. Field of the Invention

The invention relates to a method for determining or characterizing the coking tendency of baseoils and additive-treated oils.

2. Description of Background Materials

A number of standardized procedures exist for determining the coking tendencies of oils.

U.S. Pat. No. 3,248,327 discloses one test known as the Coker Detergency Test. This test is a modification of the Pratt and Whitney Test as described in United States Air Force Military Specification MIL-L-7808A. The test involves splashing the test oil in an air atmosphere against a heated aluminum panel for a given period of time and thereafter determining the amount of deposit formed on the panel. The oil is splashed onto the underside of an aluminum panel, and after a set period of time the test is stopped, and the aluminum panel is washed to remove excess non-coked oil. It is assumed that any increase in weight of the panel, after washing and drying, must be due to coke formation on the aluminum.

A similar technique is disclosed in U.S. Pat. Nos. 3,095,377 and 3,153,622, and is identified as a Panel Coker Test meeting United States Air Force specification MIL-L-9236A.

Yet another test is disclosed in U.S. Pat. Nos. 2,812,319 and 2,716,089, in which oil is heated and stirred in an aluminum measuring cup for a set period of time, after which the heated oil is permitted to settle without stirring. Thereafter the cycle is repeated a number of times, after which the oil is poured out of the cup, and the cup weighed to determine any increase in weight which would be indicative of coking.

Despite providing information as to the amount of coke which is formed, the above techniques are by their very definition imprecise and clumsy. These tests are subject to inconsistent results because of the numerous mechanical manipulations which are involved. Furthermore, none of the above techniques relies upon the measurement of asphaltenes as being an indicator of the coking tendencies of lubricating baseoils, but rather rely only upon the direct measurement of coke deposits.

SUMMARY OF THE INVENTION

Broadly, the invention is directed to a method of characterizing the coking tendency of a baseoil, by:
 (a) exposing the baseoil to conditions which accelerate asphaltene formation in the baseoil; and
 (b) testing for the onset and/or progression of asphaltene formation in the oil as a function of time.

The term "baseoil" as used throughout is taken in its broadest sense so as to include all types of oils in which one wishes to characterize coking tendency, whether the oils have been additive-treated or not.

The testing performed in step (b) may most preferably be specifically for $C_7$-asphaltene (n-heptane insolubles) formation as a function of time.

The conditioning of the baseoil may be achieved by heating and oxidation of the baseoil. The oxidation may be performed continuosly at 240–360 degrees centigrade. The oxidation is most preferably performed while sparging with an oxidizing gas. The sparging gas may be selected from the group consisting of: air, oxygen, ozone, nitric oxides, sulfur oxides, and mixtures thereof. An inert gas selected from the group of nitrogen, helium, carbon dioxide, and mixtures thereof, may be incorporated into the sparge gas.

Generally the baseoil is sparged with 1–10 standard cubic feet of air per hour. Most preferably, the baseoil is sparged with air at 4 standard cubic feet of air per hour.

So as to improve gas-liquid contact, the sparged baseoil is agitated with a mechanical agitator during heating and oxidation.

When used in conjunction with additive-treated oils the technique of the invention can be used to measure the effectiveness of the additive. To achieve this, the method comprises the steps of:
 (a) exposing a first sample of the baseoil (without additive) to conditions which accelerate asphaltene formation in the baseoil;
 (b) testing for the onset and/or progression of asphaltene formation in the exposed baseoil as a function of time;
 (c) incorporating the additive into a second sample of the baseoil before exposure;
 (d) exposing the baseoil of step (c) having the additive incorporated therein under conditions substantially identical to step (a);
 (e) testing for the onset and/or progression of asphaltene formation in the exposed baseoil of step (d) as a function of time under substantially identical conditions to step (b); and
 (f) comparing the onset times and/or formation rates measured in steps (b) and (e).

The baseoils, with and without additive, are exposed substantially identically by oxidizing and heating the baseoils, preferably with oxygen sparging at 240–360 degrees C. In one embodiment the oils of steps (a) and (d) are sparged with air at about 4 standard cubic feet of air per hour while mechanically agitating the oils.

According to an alternative embodiment the baseoil is continuously oxidized on the exposed surface of a heated cylinder rotating within the sample baseoil. The temperature to which the cylinder is heated depends on whether or not catalyst is being used.

The invention is not limited as to the specific technique which is used to accelerate asphaltene formation, and specifically $C_7$-asphaltene formation, and may, for example, extend to other conditioning methods, e.g., the oils may be conditioned catalytically. When conditioning catalytically, catalysts are selected from the group consisting of: ferric chloride hexahydrate; cobalt octoate; iron naphthenate, stannic chloride and other oxidation catalysts, and mixtures thereof.

The invention is further directed to adding a compound selected from the group consisting of peroxides, hydroperoxides, oxidized lube oils and mixtures thereof. When added in effective amounts these substances serve to reduce asphaltene reaction times and temperatures, thereby further accelerating asphaltene formation in the baseoils. The compound is added in an amount of about 0.1 to about 0.5 per hundred weight of the lube oil.

BRIEF DESCRIPTION OF DRAWINGS

FIG. 2a illustrates an apparatus for accelerating oxidation of the baseoil;

FIG. 2c shows a side view of the sparger;

DETAILED DESCRIPTION OF THE INVENTION

Figure 1:
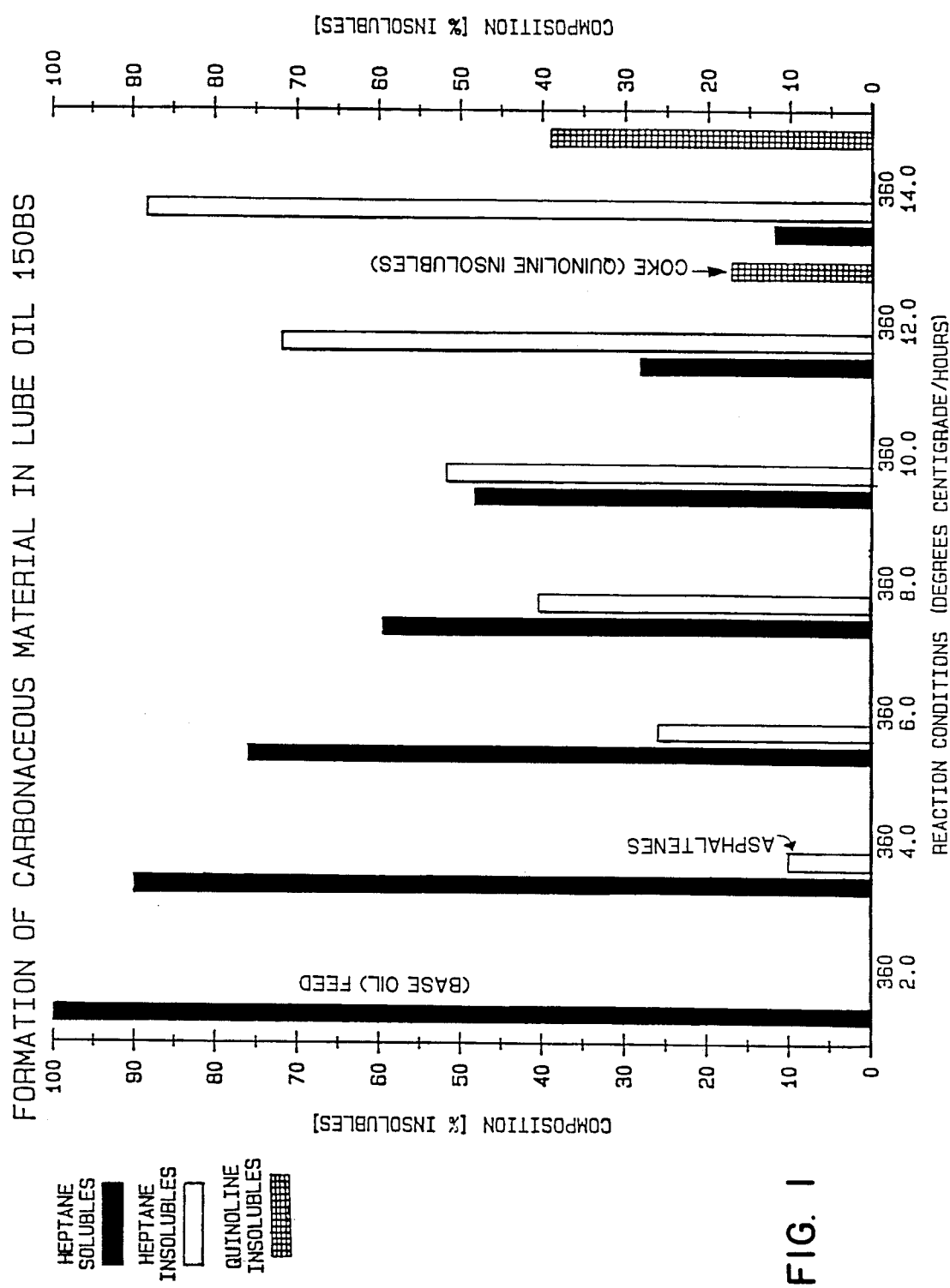
FIG. 1 illustrates the progression of asphaltene and coke (quinoline insolubles) formation in a baseoil as a function of time at constant temperature.

Analysis of used lube oils from engine tests and the carbonaceous materials from engine piston walls indicates that these materials have very high oxygen content. 2-3 wt % of oxygen was found in the used lube oils, and 25-35 wt % of oxygen was found in the carbonaceous deposit material on the piston walls.

High oxygen content in the oil and the carbonaceous material indicates that oxidative—polymerization of the baseoils is one of the major causes responsible for the formation of the carbonaceous material in the lube oil and the deposition on the wall of the piston. This is also consistent with the stirring and splashing which were required in previous characterization techniques, since agitation in the presence of air results in oxidation of the oil.

Further investigation of the mechanism of the carbon formation in lube oils led to the discovery that, on air oxidation of a baseoil, paraffin-insoluble compounds—asphaltenes—are the first molecular species formed in the baseoils upon oxidation, and that these asphaltenes are transformed gradually into carbonaceous material containing high infusable coke (quinoline insolubles). Amongst the wide range of paraffin insolubles which are formed upon heating and oxidation, the heptane insolubles, hereinafter designated as $C_7$-asphaltenes, are of particular interest.

Asphaltenes generally are composed of carbon, hydrogen, oxygen, sulfur with a C:H atomic ratio of 1.0–1.5 and average molecular weight of about 250–1000. They are brownish solids with melting points of 100–400 degrees centigrade, with extremely high tendency to coke formation at 200–300 degrees centigrade in a non-oxygen nitrogen atmosphere with a coke yield of 35–55% over 2 hrs. The asphaltenes have a decomposition temperature of about 400 degrees centigrade as determined by thermogravimetric analysis in nitrogen (heating rate 10 degrees C./minute).

Asphaltenes are molecules of high molecular weight, on the order of Mn=1000, which upon mild heating at temperatures as low as 200 degrees Centigrade will dehydrogenate and polymerize into higher molecular weight species such as coke (quinoline insolubles).

During oxidative-polymerization of the baseoil at high temperatures, e.g., 240–360 degrees C., portions of the baseoils will react with oxygen and other oxidizing agents, e.g., sulfur, leading to polymerization and introduction of various oxygen functional groups such as phenolic, hydroxyl, carboxyl, ketones, aldehydes, ethers, etc. Other polar atoms such as sulfur and nitrogen are also present. These high molecular weight, highly oxidized molecules become insoluble in aliphatic solvents and can be determined quantitatively as the insolubles in paraffinic solvents. This insoluble portion is referenced herein as asphaltenes. When n-heptane is used as a solvent, the n-heptane insoluble portion is called $C_7$-asphaltene.

Asphaltenes may be specified with reference to the particular paraffins in which they are insoluble, e.g., n-heptane, n-hexane, n-pentane, isopentane, petroleum ether, etc. For purposes of this application, particular reference is made to $C_7$-asphaltenes as being the preferred indicator for coke characterization purposes.

Figure 6:
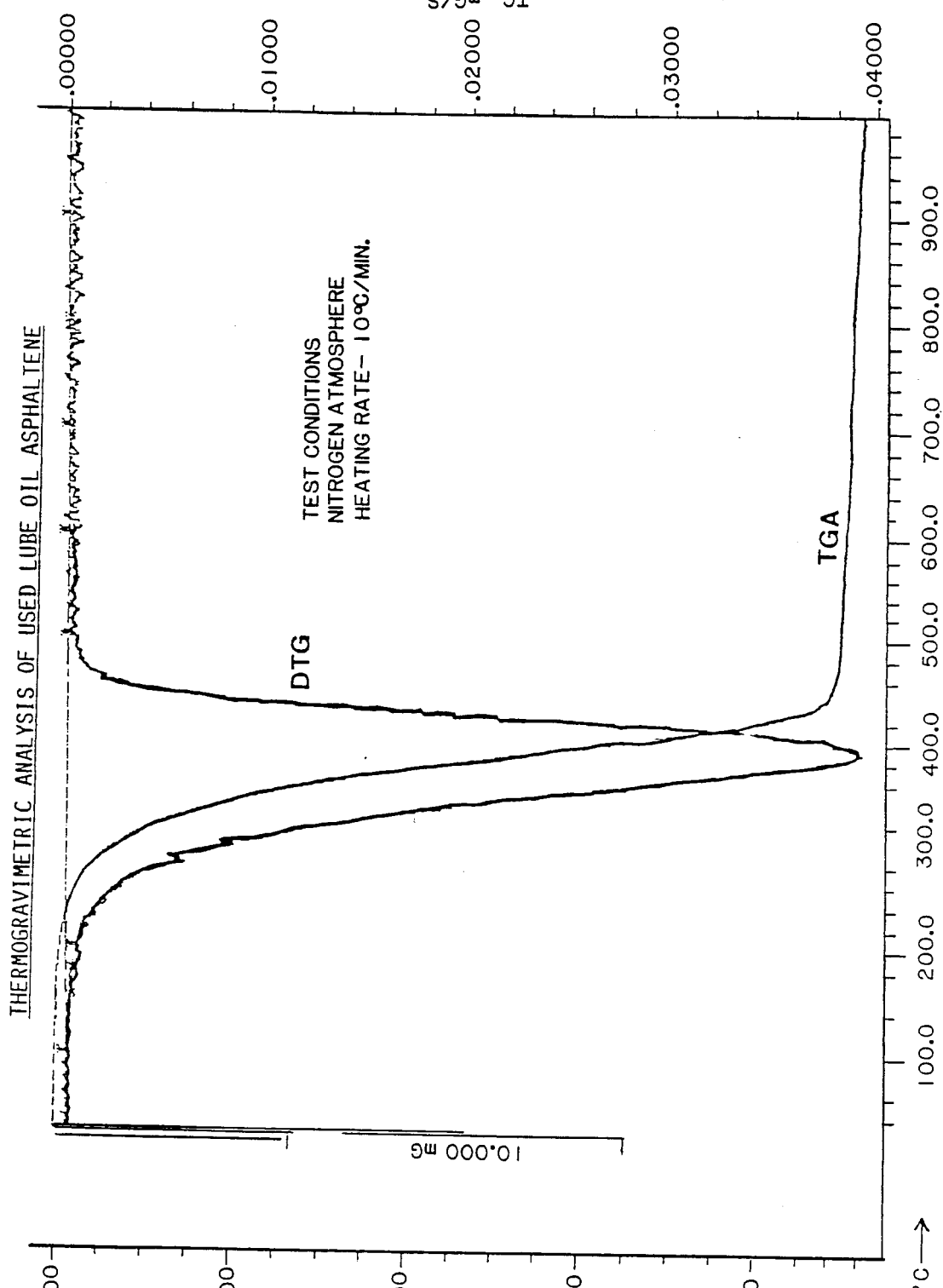
FIG. 6 illustrates the thermogravimetric analysis of used oil asphaltene.

The $C_7$-asphaltene formed when oxidizing lube baseoil is defined as the insolubles in paraffinic solvents and more specifically the insolubles in n-heptane. Therefore, asphaltenes represent a solubility class of compounds. One method of characterizing asphaltenes is by thermogravimetric analysis (TGA). The thermogram of our $C_7$-asphaltenes is presented in FIG. 6 (showing maximum decomposition at about 400 degrees C.).

The carbonization of asphaltenes into various carbonaceous products and coke is known, for example, see U.S. Pat. No. 4,518,483, the disclosure of which is incorporated by reference, which teaches a process for carbonizing asphaltenes into carbon precursors useful for carbon fiber production.

The formation in an initially asphaltene-free baseoil (150 BS) of $C_7$-asphaltene and quinoline insolubles (coke) on subjecting the baseoil to air-oxidation at 360° (oil temperature) is illustrated graphically in FIG. 1. The transition from lube baseoil to substantially asphaltene (about 75%) prior to the onset of coke formation should be noted.

Figure 4:
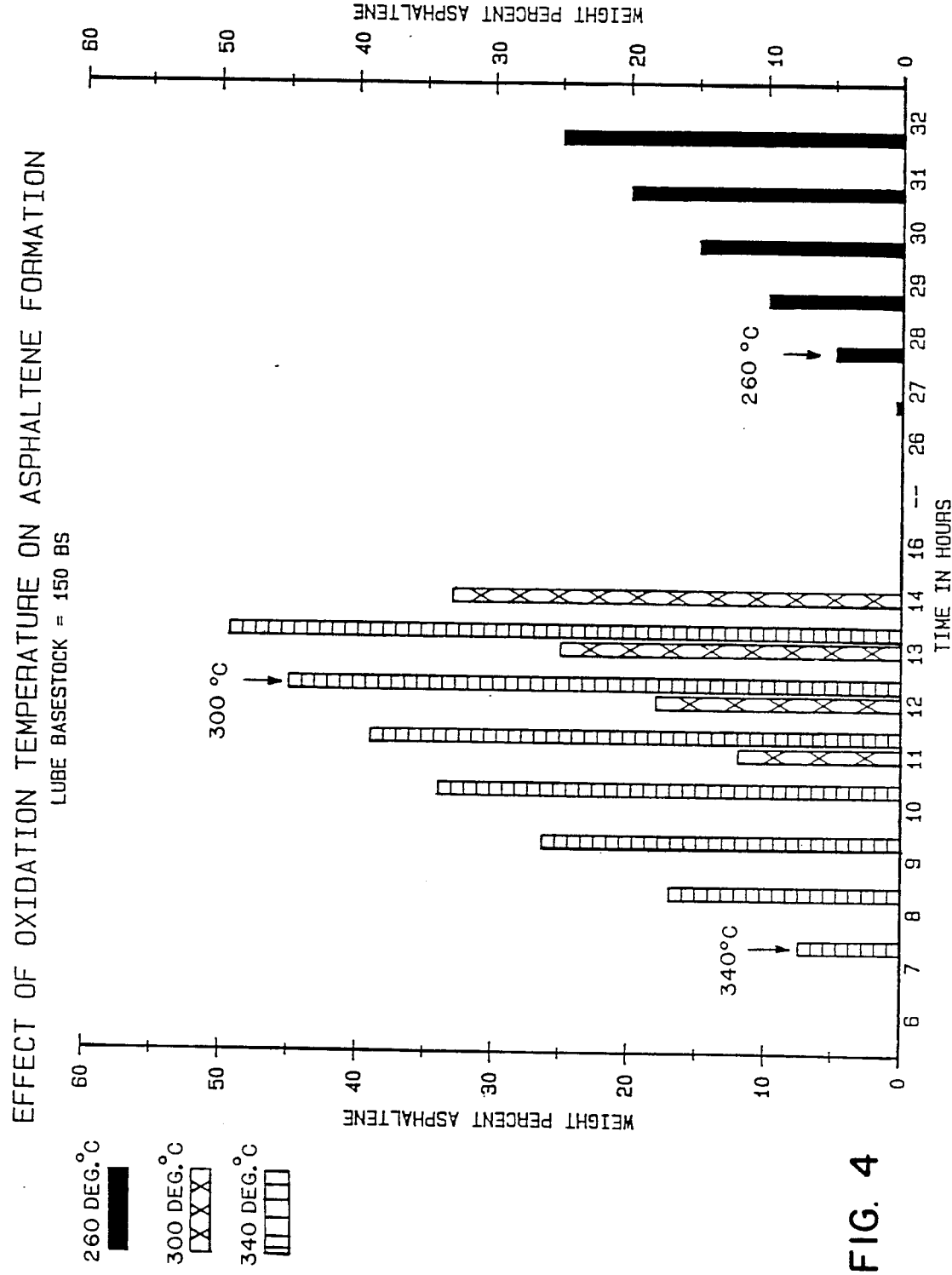
FIG. 4 illustrates the acceleration in onset of asphaltene formation as a function of temperature to which the baseoil is heated.

As further proof of the relationship between asphaltene and coking, reference is made to FIG. 4 in which it is seen that as temperature increases, the onset of asphaltene formation, as is the case with coke formation, is accelerated.

Realizing that $C_7$-asphaltenes, and particularly normal heptane-insoluble $C_7$-asphaltenes, are the first molecular species formed when oxidizing a baseoil and that $C_7$-asphaltenes are the real precursors for coke formation in the bulk of the lube oil and on the piston wall has led to the discovery of the inventive method for characterizing the coking tendency of baseoils and additive-treated baseoils, thus making it possible to rapidly and more reliably obtain valuable information on oil coking characteristics and additive performance.

The inventive method provides an accelerated, inexpensive and highly scientific method for characterizing baseoils and the efficacy of additives.

Basically, the inventive method for characterizing baseoils and additive-treated baseoils involves two steps:

a. Oxidizing the baseoil continuously at an elevated temperature, most preferably on the order of 240°–360° C.; and b. Continuously determining the $C_7$-asphaltene content in the oxidized lube baseoils over a period of time such that the rate of $C_7$-asphaltene formation may be determined.

The time required to form $C_7$-asphaltenes in the baseoils under accelerated conditions is related to the relative chemical reactivity of the baseoils. Baseoils which require a short time (a few hours) when using the inventive accelerated oxidation process have a relatively high tendency for coke formation. On the other hand, baseoils which require a very long time (10–20 hours) to form asphaltenes, and $C_7$-asphaltenes in particular, have relatively high chemical stability and a lower tendency for coke formation.

According to the invention it is possible to rely upon asphaltene formation for characterization purposes by detecting the onset of its formation, as well as by following the progress of formation of the asphaltenes. Either one or both techniques, depending upon the circumstances, may be useful to provide characterization information.

ACCELERATED OXIDATION PROCEDURE

So as to permit rapid characterization, the invention provides for performing oxidation in an accelerated manner. According to one embodiment of the invention, illustrated in FIG. 2a, the accelerated oxidation process of the invention is performed by heating a baseoil or additive-treated oil in a system wherein baseoil, maintained under an inert nitrogen floating (blanketing) seal in reactor 1a, is aerated by means of a specially designed sparger which includes a sparger ring 2 and sparger tube 3, and heated to a specified temperature, controlled by thermocouple 7. A high-speed (500–600 RPM) mechanical agitator 5 run by a motor 6 and a rod 4, which is essential for gas-liquid reactions, insures maximum liquid-gas contact. A condensation reflux system 8 including a distillate receiver vent 11, for condensing volatilized hydrocarbons is also provided. Samples are routinely withdrawn and checked for paraffinic-insoluble content (asphaltenes).

Figure 2B:
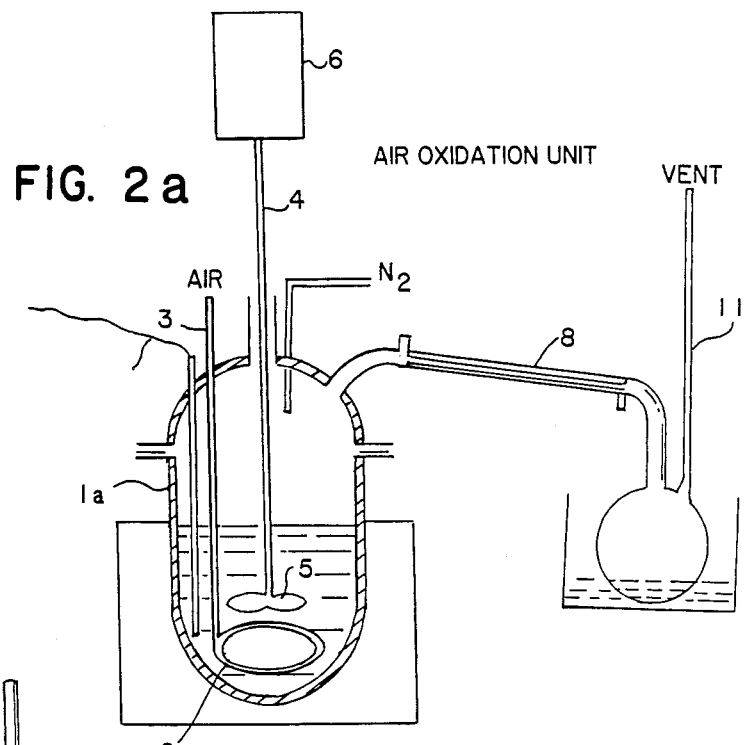
FIG. 2b illustrates a sparger which is useful in performing the process of the invention.
Figure 2B:
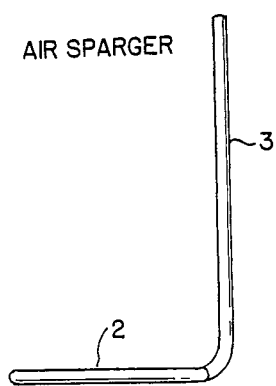
Figure 2B:
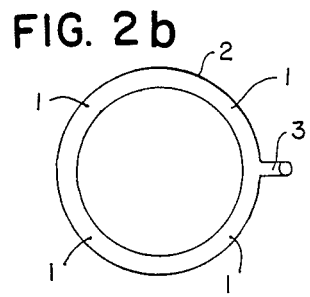

As shown in FIGS. 2b and 2c the sparger includes sparger tube 3 and four orifices 1 equiangularly distributed on the upper surface of the sparger ring 2. The upper surface of the sparger ring is located approximately 1 inch beneath the agitator blades 5.

In a typical oxidation experiment 800 grams of the baseoil is introduced into a 1 liter reaction flask. The baseoil is then heated to the desired temperature with continuous air sparging at the bottom of the reactor at a rate=4 SCFH. The baseoil is agitated vigorously using a high-speed mechanical agitator at 560 RPM.

According to another embodiment of the invention one or more catalysts selected from the group of: ferric chloride hexahydrate, stannic chloride, and/or other appropriate catalysts in total amounts by weight of about 0.25% catalyst/feed, may be added, after which the sample being tested is heated to about 180–280 degrees C. While such a system does accelerate oxidation, it represents a less accurate simulation of actual operating conditions by virtue of the presence of the catalyst and the use of lower reaction temperature.

Figure 7:
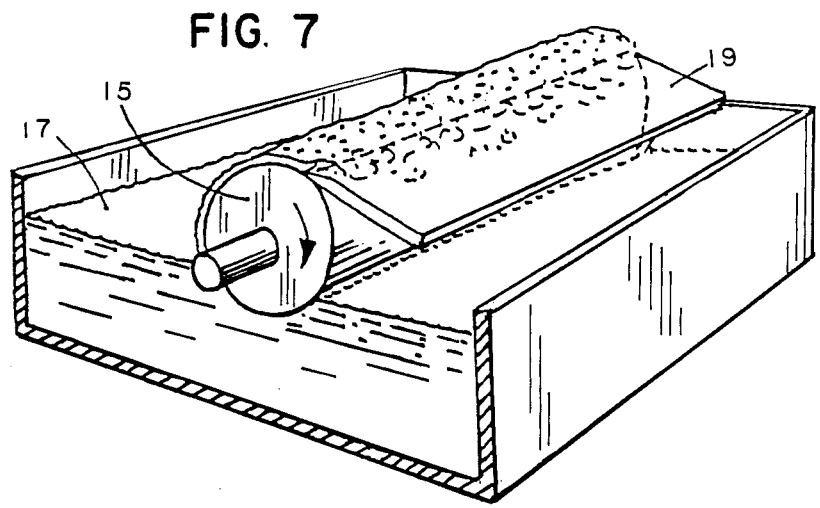
FIG. 7 illustrates an apparatus for commercially measuring asphaltene buildup.

In a more commercial technique, the oil being sampled is characterized in an apparatus of the type shown in FIG. 7. In this apparatus a cylinder 15, heated to a temperature of 240°–260° C., is partially submerged in an oil sample reservoir 17. The upper surface of the cylinder is progressively exposed to air as it is rotated. Depending upon the parameters of the analysis the cylinder is either scraped continuously or intermittently by means of a doctor blade 19. As previously, parameters and times may be varied by the use of catalyst in the oil. When using a catalyst temperatures as low as 180°–280° C. may be used.

SAMPLING AND ANALYSIS TECHNIQUE

According to one possible analysis technique, samples of the oxidized baseoil are taken and the $C_7$-asphaltene content is determined by extraction with n-heptane under the following condition:

Solvent = n-heptane
Solvent: oxidized baseoil = 1.0:50
Extraction temperature (°C.) = 104–108
Extraction time (hours) = 2.0
Filtration = Frittered glass (4–5 micron)
Drying = 50°–60° C./4 hours Presence and extent of asphaltenes is determined by comparing the weight of the filter before and after filtration.

CHARACTERIZATION

The inventive method for characterizing the coking tendency of untreated baseoil and additive-treated lubricating oils is illustrated in the following examples. The characterization itself may take the form of either measuring the onset of asphaltene formation, its formation as a function of time, or both, depending upon the standards established for the test.

EXAMPLES 1–4

Asphaltene formation in untreated baseoils

Figure 3:
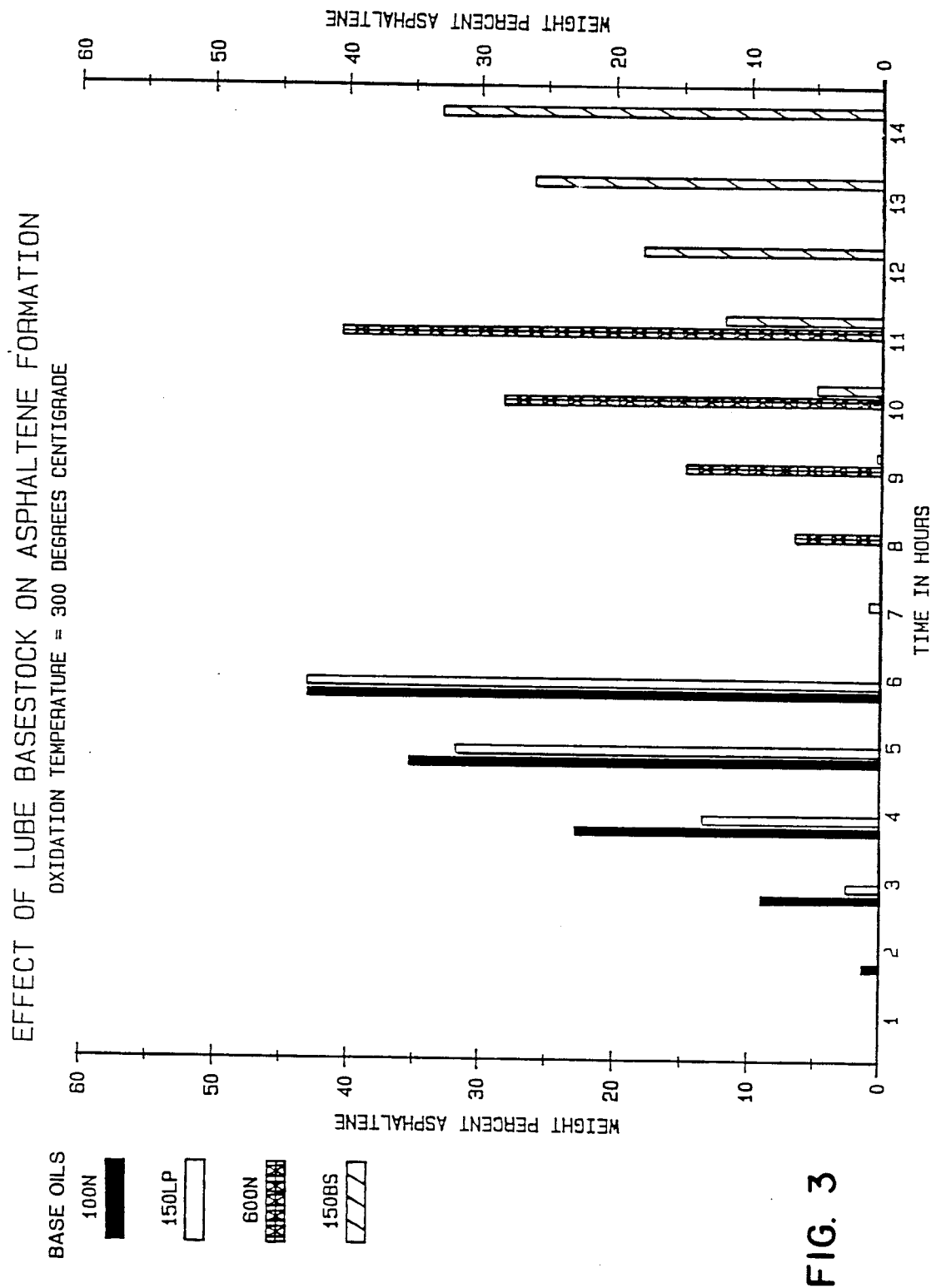
FIG. 3 illustrates the amounts of measured asphaltenes formed in different baseoils, with all other parameters being kept constant.

Four baseoils obtained by vacuum distillation of vacuum residues are subjected to the accelerated oxidation process described above (without catalyst present). The baseoils are oxidized at 300° C. The asphaltene content is determined on samples obtained hourly and analyzed by the above method. The rate of $C_7$-asphaltene formation varies depending on the type and characteristics of baseoil used. Examples 1, 2, 3 and 4 (FIG. 3) illustrate the $C_7$-asphaltene formation for the four baseoils.

EXAMPLES 5, 6 and 7

Effect of oxidation temperature on $C_7$-asphaltene formation

A baseoil (150 BS) obtained by vacuum - distillation is subjected to the above accelerated oxidation process at three oxidation temperatures (260° C., 300° C. and 340° C.) to obtain information on the effect of oxidation temperature on $C_7$-asphaltene formation (Examples 5, 6 and 7). FIG. 4 graphically illustrates the effect of oxidation temperature on asphaltene formation in 150 BS baseoil.

The data clearly establishes that $C_7$-asphaltene formation is dependent on oxidation temperature, and that higher oxidation temperature leads to higher rate of asphaltene formation. This is consistant with the technical literature which indicates that increased liquid temperature leads to increased coke and asphaltene formation.

EXAMPLES 8, 9, 10 and 11

Asphaltene formation in additive-treated baseoils

A baseoil (150 BS) is treated with three additives commercially used in automotive lubricating oil production. These additives are ECA9001A, (nonyl phenyl sulfide) and PARANOX 16 (zinc dialkyl dithiophosphate) and PARANOX 106 (dispersant comprised of the borated reaction product of polyisobutenyl succinic anhydride and polyamine). The treated baseoils are then subjected to the above accelerated oxidation conditions at 300° C. The $C_7$-asphaltene content is determined hourly.

The additive-treated baseoils show reduced tendency for $C_7$-asphaltene formation relative to untreated baseoils, thus indicating the efficacy of the additives in reducing asphaltene and coke formation in the engine. Examples 9, 10 and 11 give the asphaltene formation rate when oxidizing additive-treated baseoils in comparison to the untreated baseoil (Example 8). The effect of additive on asphaltene formation is presented graphically in FIG. 5.

Figure 5:
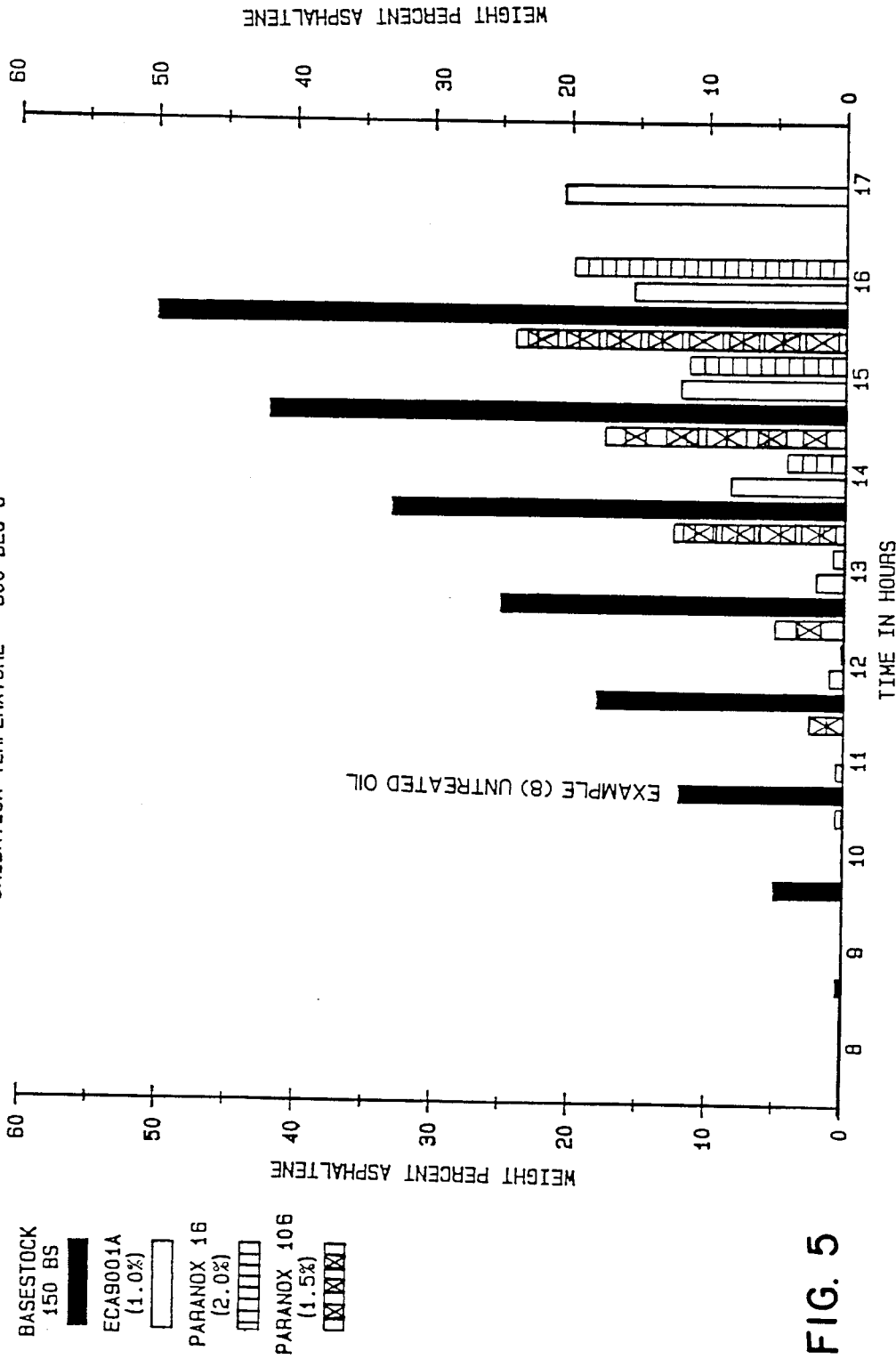
FIG. 5 illustrates how the characterization technique of the invention is used to characterize the effects of various additives on asphaltene formation.

FIG. 5 shows the value of the characterization technique of the invention which may be used rapidly to determine the effects of additives on asphaltene and coke formation rates.

Although the invention has been described with reference to particular means, materials and embodiments, the invention in not so limited. For example, the invention extends to the use of any characterization procedure which may be utilized to follow $C_7$-asphaltene formation in baseoils, whether catalytic or otherwise.

Additionally, the manner in which the data on asphaltene formation is collected or collated is insignificant for purposes of the invention provided that the result permits one to follow $C_7$-asphaltene formation as a function of time whereby the oxidative tendency of the baseoil may be determined.

What is claimed is:

1. A method of characterizing the coking tendency of baseoil comprising the steps of:
   (a) subjecting said baseoil to conditions which accelerate asphaltene coke precursor formation in said baseoil, and
   (b) characterizing the coking tendency of the baseoil by determining (i) the onset and progression of asphaltene coke precursor formation as a function of time or (ii) the progression of asphaltene coke precursor formation as a function of time, wherein a faster onset of asphaltene coke precursor formation and a higher rate of aphaltene coke precursor formation or a higher rate of asphaltene coke precursor formation indicates a higher coking tendency of the baseoil than a slower onset of asphaltene coke precursor formation and a lower rate of asphaltene coke precursor formation or a lower rate of asphaltene coke precursor formation.

2. The method as defined by claim 1 wherein in step (b) said asphaltene coke precursor is $C_7$-asphaltene.

3. The method is defined by claim 2 wherein step (a) comprises subjecting said baseoil to oxidizing conditions.

4. The method as defined by claim 2 wherein step (a) comprises subjecting said baseoil to heat.

5. The method as defined by claim 2 wherein step (a) comprises subjecting said baseoil to heat and oxidizing conditions.

6. The method as defined by claim 5 wherein step (a) comprises subjecting said baseoil to oxidizing conditions at about 240–360 degrees centigrade.

7. The method as defined by claim 6 wherein subjecting said baseoil to oxidizing conditions comprises sparging said baseoil with an oxidizing gas.

8. The method as defined by claim 7 wherein said oxidizing gas is selected from the group consisting of air, oxygen, ozone, nitric oxides, sulfur oxides, and mixtures thereof.

9. The method as defined by claim 8 further comprising incorporating inert gas into said oxidizing gas, said inert gas being selected from the group consisting of nitrogen, helium, carbon dioxide, and mixtures thereof.

10. The method as defined by claim 8 further comprising agitating said baseoil during sparging with a mechanical agitator.

11. The method as defined by claim 1 wherein step (b) is carried out by measuring the concentration of asphaltene coke precursor in said baseoil as a function of time.

12. The method as defined by claim 1 wherein said baseoil is additive-treated with at least one additive effective to reduce coking.

13. A method of characterizing the coking tendency of baseoil comprising the steps of:
    (a) subjecting said baseoil to conditions which catalytically accelerate asphaltene coke precursor formation in said baseoil; and
    (b) characterizing the coking tendency of the baseoil by determining (i) the onset and progession of asphaltene coke precursor formation as a function of time or (ii) the progression of asphaltene coke precursor formation as a function of time, wherein a faster onset of asphaltene coke precursor formation and a higher rate of asphaltene coke precursor formation or a higher rate of asphaltene coke precursor formation indicates a higher coking tendency of the baseoil than a slower onset of asphaltene coke precursor formation and a lower rate of asphaltene coke precursor formation or a lower rate of asphaltene coke precursor formation.

14. The method is defined by claim 13 wherein in step (b) said asphaltene coke precursor is $C_7$-asphaltene.

15. The method as defined by claim 14 wherein step (a) comprises catalytically accelerating asphaltene formation by subjecting said baseoil to a catalyst selected from the group consisting of ferric chloride hexahydrate, cobalt octoate, iron naphthenate, stannic chloride, and mixtures thereof.

16. The method as defined by claim 15 wherein step (a) further comprises heating said baseoil at a temperature of 180°–280° C.

17. The method as defined by claim 13 wherein step (a) comprises sparging said baseoil with an oxidizing gas selected from the group consisting of air, oxygen, ozone, nitric oxides, sulfur oxides, and mixtures thereof.

18. The method as defined by claim 17 comprising incorporating an inert gas into said oxidizing gas, said inert gas being selected from the group consisting of nitrogen, helium, carbon dioxide, and mixtures thereof.

* * * * *